(12) United States Patent
Pagés Pinyol

(10) Patent No.: US 7,622,078 B2
(45) Date of Patent: Nov. 24, 2009

(54) APPARATUS FOR THE AUTOMATED CLINICAL ANALYSIS OF SAMPLES

(75) Inventor: Josep Pagés Pinyol, Barcelona (ES)

(73) Assignee: Grifols, S.A., Barcelona (ES)

( * ) Notice: Subject to any disclaimer, the term of this patent is extended or adjusted under 35 U.S.C. 154(b) by 815 days.

(21) Appl. No.: 11/270,346

(22) Filed: Nov. 8, 2005

(65) Prior Publication Data

US 2006/0104862 A1 May 18, 2006

(30) Foreign Application Priority Data

Nov. 18, 2004 (ES) ................... 200402773

(51) Int. Cl.
G01N 21/00 (2006.01)
(52) U.S. Cl. .............. 422/64; 422/63; 422/65; 422/66; 422/67; 436/43
(58) Field of Classification Search .......... 422/63–68.1
See application file for complete search history.

(56) References Cited

U.S. PATENT DOCUMENTS

| 3,916,157 | A | 10/1975 | Roulette et al. |
| 4,808,380 | A | 2/1989 | Minekane |
| 5,314,825 | A | 5/1994 | Weyrauch et al. |
| 5,651,941 | A | 7/1997 | Stark et al. |
| 6,984,527 | B2* | 1/2006 | Miller ..................... 436/180 |
| 2003/0089581 | A1* | 5/2003 | Thompson et al. .......... 198/619 |
| 2003/0194349 | A1* | 10/2003 | Carey et al. .................. 422/63 |
| 2004/0208785 | A1* | 10/2004 | Seto et al. .................... 422/58 |

* cited by examiner

*Primary Examiner*—Jill Warden
*Assistant Examiner*—Jameson Q Ma
(74) *Attorney, Agent, or Firm*—Darby & Darby, P.C.

(57) ABSTRACT

The apparatus comprises an assembly of modules functionally interrelated with one another, and controlled by means of a central control unit in an embodiment of circular type in concentric rings of a reagent module and a rotatory carousel carrying the incubation reaction containers, with adjacent and external arrangement of a module for feeding the disposable reaction containers by means of detachable racks and a scanning device likewise concentric with the carousel, combining with a unit for feeding by pushing the reaction containers from the racks towards the grooves of the incubation carousel, and of two displacement arm devices.

11 Claims, 14 Drawing Sheets

APPARATUS FOR THE AUTOMATED CLINICAL ANALYSIS OF SAMPLES

The present invention is intended to disclose an apparatus for the automated clinical analysis of samples which provides significant characteristics of novelty and inventive step with respect to the prior art.

The apparatus basically comprises an entry module for reaction containers, an entry module for samples, a reagent store, a sample transport arm device, a reagent arm device and a scanning device. These modules carry out functions associated with one another and coordinated by a central control unit, interacting with one another in a random manner and with an incubator, remaining adjacent to the latter.

The entry of reaction containers takes place through a zone through which the operator introduces into the system the disposable reaction containers on which dispensing and the reactions will be carried out. It is located adjacent to the incubator and outside same, preferably comprising two seats, each one for a support or rack of reaction containers, and in the shape of respective arcs of circumference that are concentric with the incubator and with a loading device equipped with a pusher for the reaction containers.

The entry for samples is the zone through which the operator introduces individually the primary tubes for analysing and collects the processed tubes. It is separate from the incubator and has a continuous loading system capable of presenting all the tubes, one by one, at a specific position which is the pipetting point, where the sample is drawn up, and maintaining them in a recirculation zone in case it is necessary to repeat or increase the number of analyses and return the tubes already dealt with to a specific area of the entry.

A sample arm device is intended to link the sample entry with the incubator, being capable of dispensing the sample in one or more positions of said incubator and by rotation of the latter, in any reaction container.

A reagent store is constituted in the shape of a circular ring internally concentric with the incubator, containing a plurality of removable small steps provided with circular movement for housing reagents and diluents for the analysis of samples.

A reagent arm device is located inside the reagent store, having freedom of movement according to a system of polar co-ordinates, that is, radial and angular, thereby making it possible to have access to any position in the reagent store.

The reader device has a body in the shape of a circular ring externally concentric with the incubator, preferably having a multiplicity of seats for reaction containers in the form of channels arranged radially in order to allow the introduction of the reaction containers from the incubator and their exit through the other end. The device is provided with a lid (not shown) on its upper part which can be partially uncovered in order to permit the dispensing of additional reagents.

The apparatus is completed by means of various secondary elements which, on a non-limiting basis, are listed below:
  tanks for the solutions for washing the probes
  tanks for waste liquids
  tanks for storing the used reaction containers
  a fluid system for providing the two probes (for samples and for reagents) with the capacity for suction and measured dosing, as well as washings
  electronic systems and computer for controlling each of the elements touch screen for interface with the user
  system for intercommunication with the host For greater understanding thereof, some drawings showing a preferred embodiment of the present invention are appended hereto by way of non-limiting example.

Figure 14:
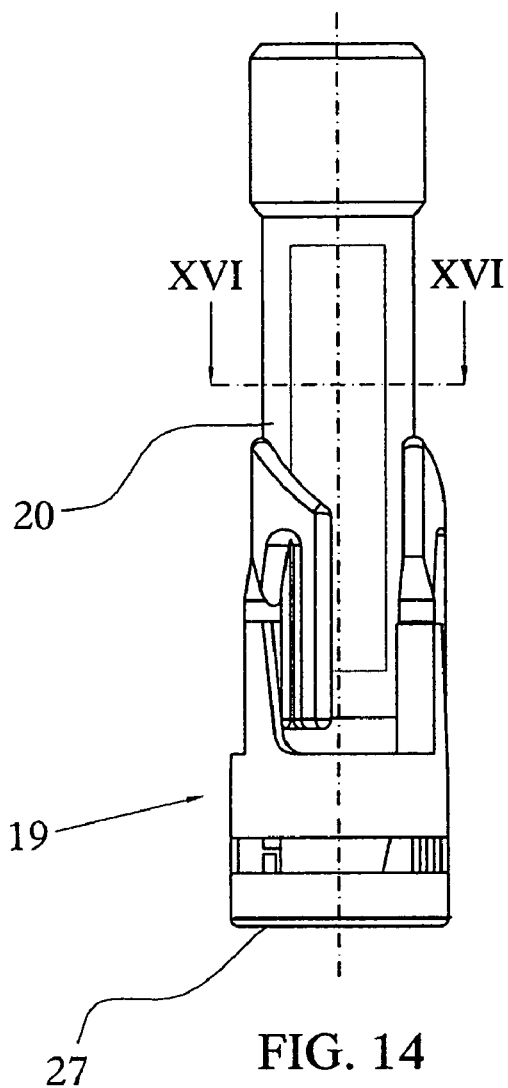
Figure 15:
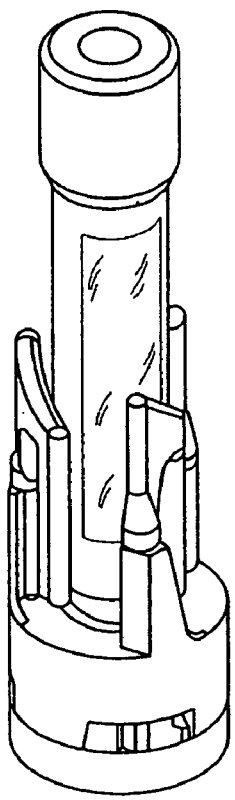

FIGS. 14 and 15 respectively show a view in side elevation and a perspective view of the support for samples, with a tube of samples mounted therein.

Figure 16:
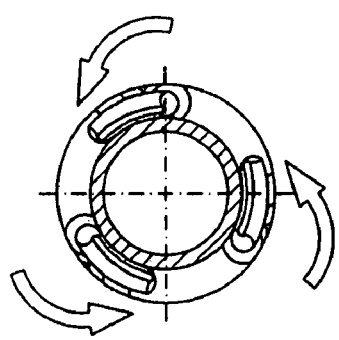

FIG. 16 shows a section through the section plane shown in FIG. 14.

Figure 17:
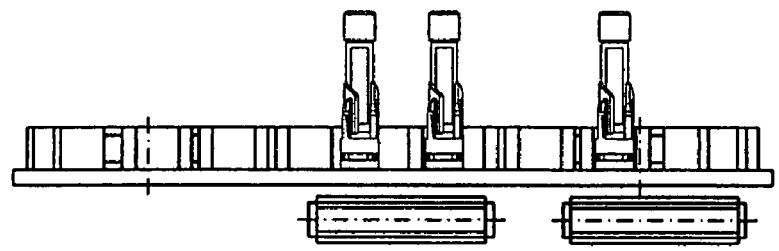
Figures 18, 19:
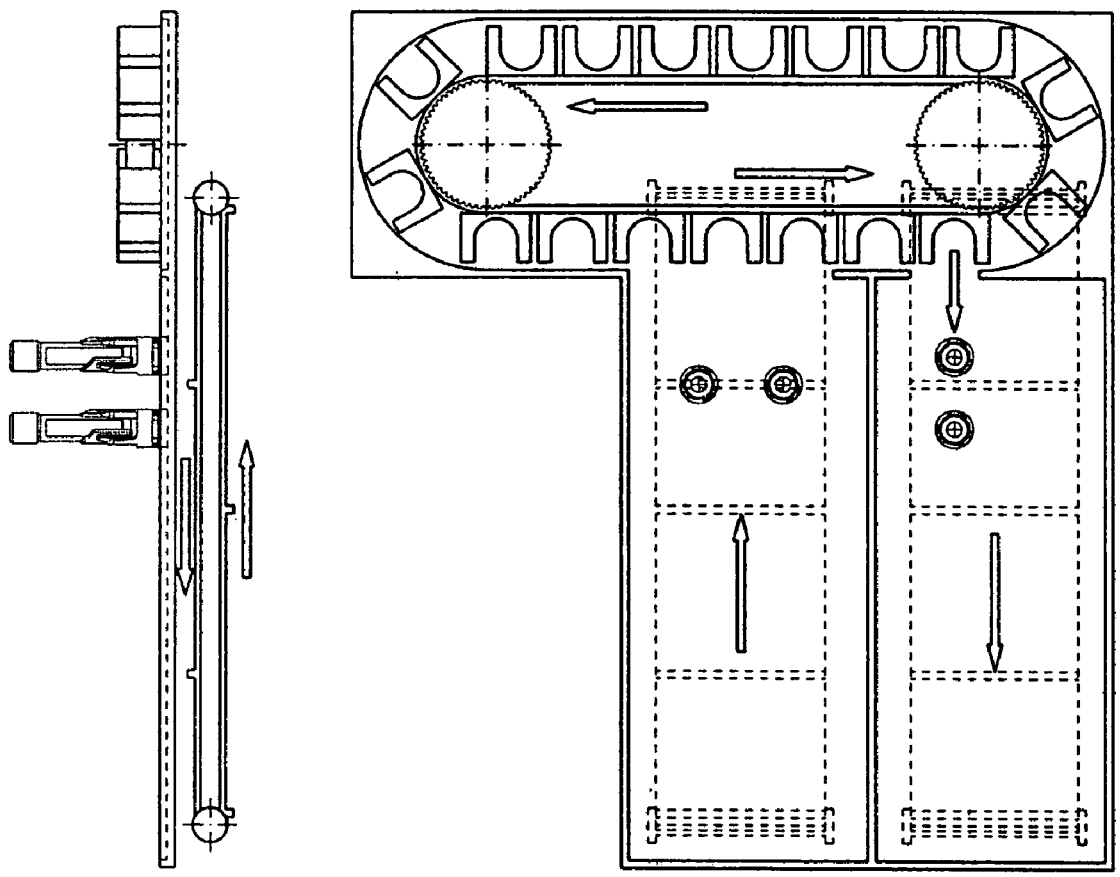

FIGS. 17, 18 and 19 show respective details of the magnetic sample entry device.

Figure 20:
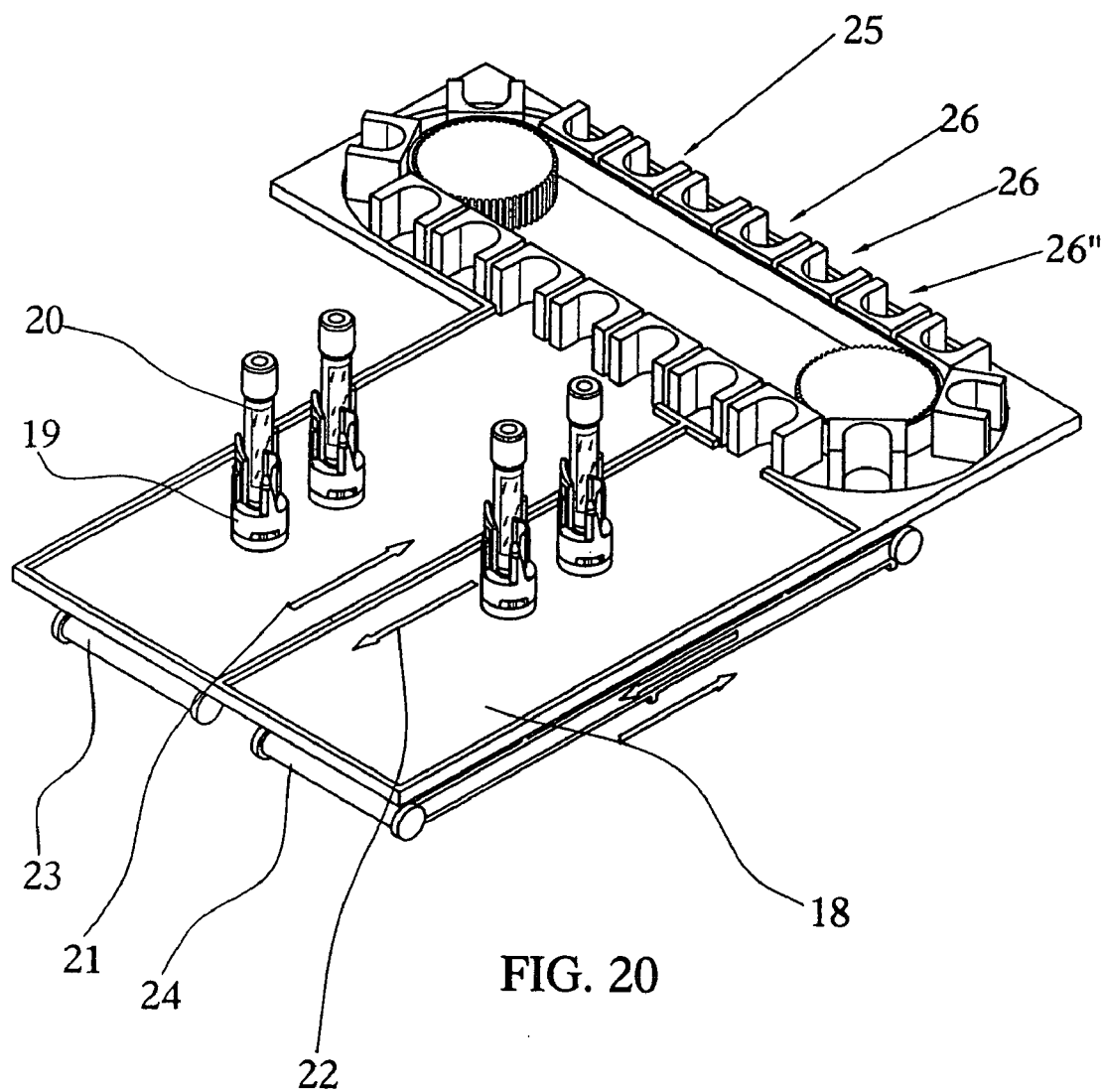

FIG. 20 shows a perspective view of the same sample entry assembly.

Figures 21, 22:
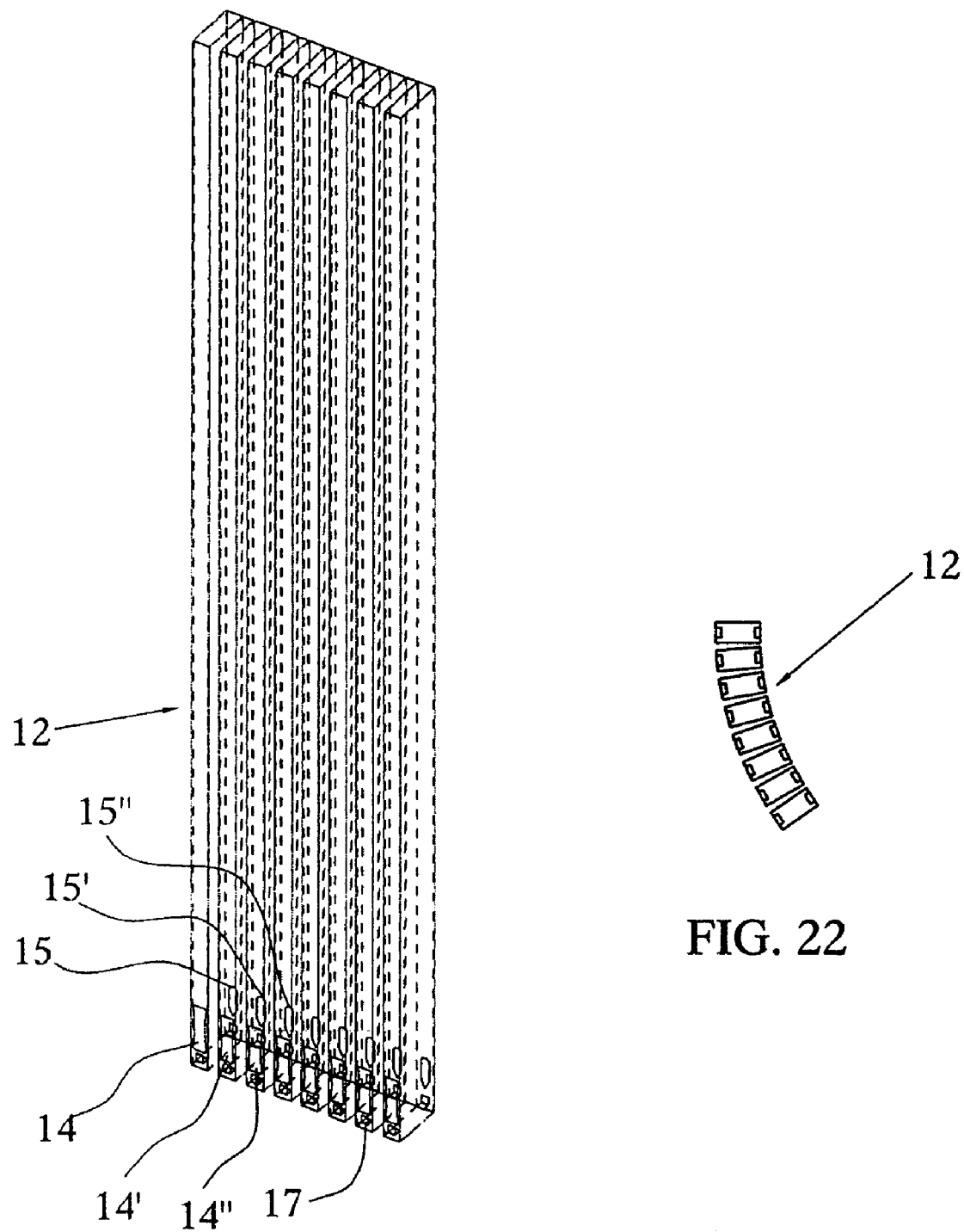

FIGS. 21 and 22 show a perspective view and a plan view in an arcuate position of a rack for reaction containers.

Figure 1:
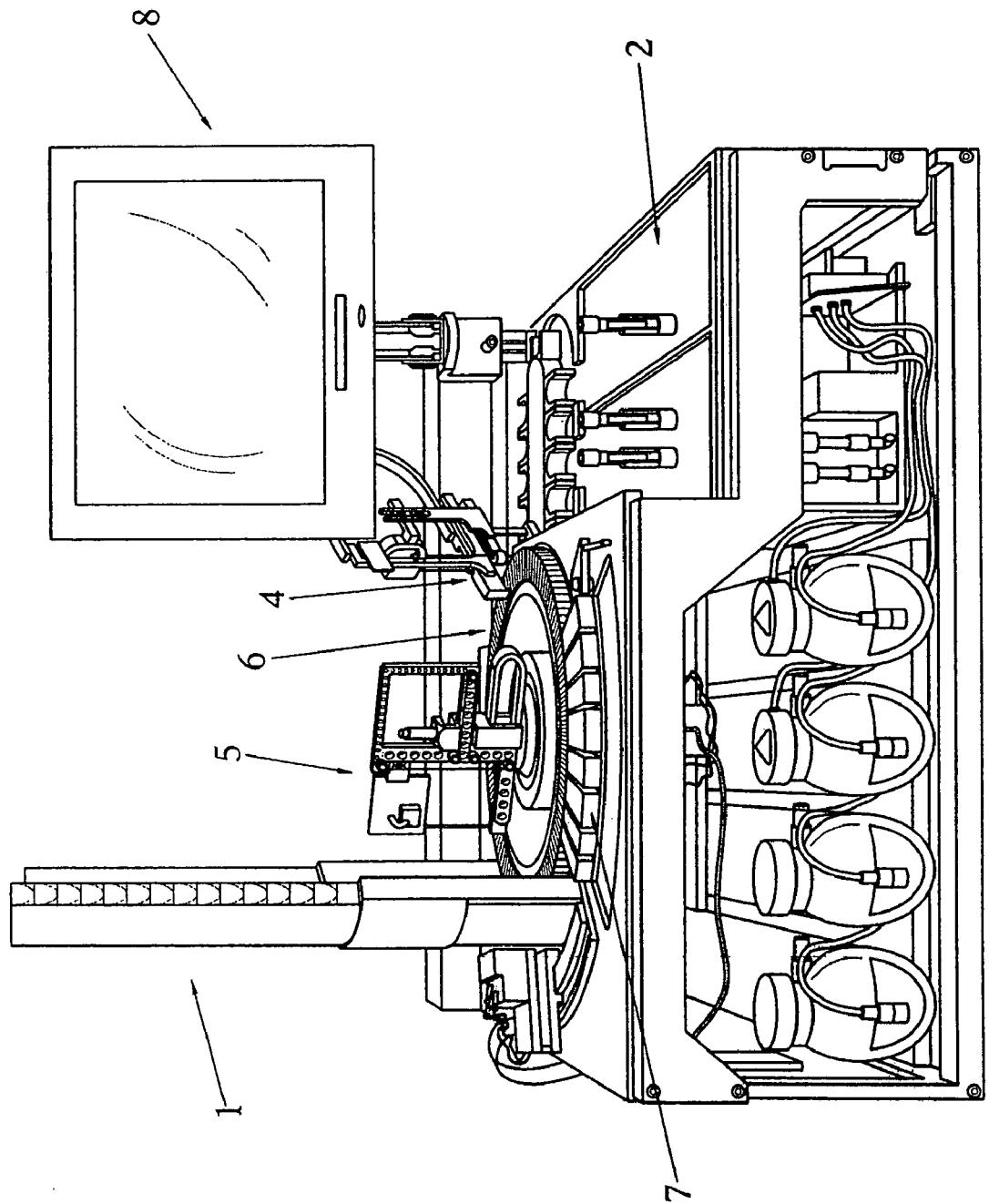
FIG. 1 shows a perspective view of an apparatus according to the present invention, from the front part.
Figure 2:
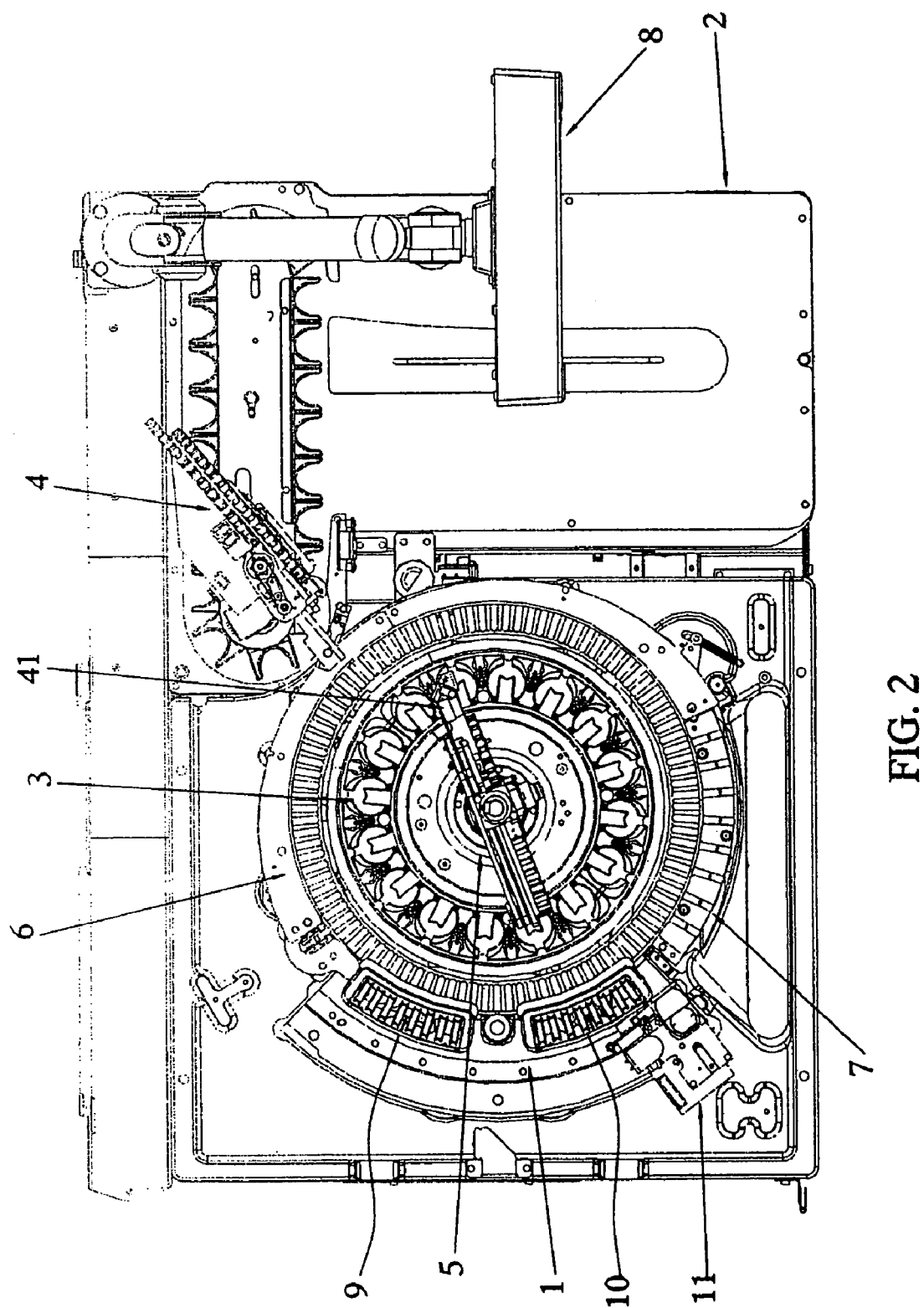
FIG. 2 shows a plan view of the same apparatus shown in FIG. 1.
Figure 3:
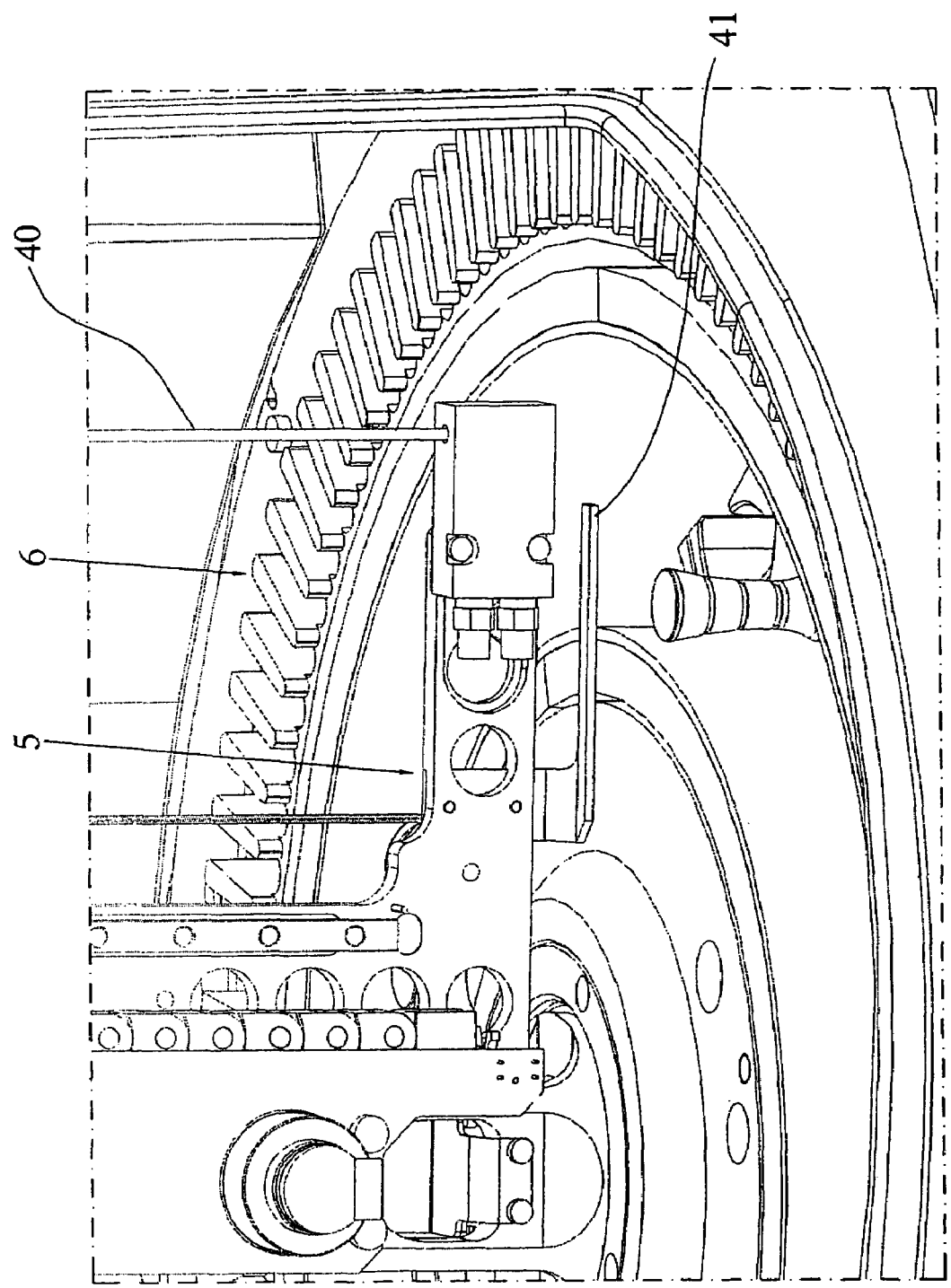
FIG. 3 shows a detail of the reagent arm.
Figure 4:
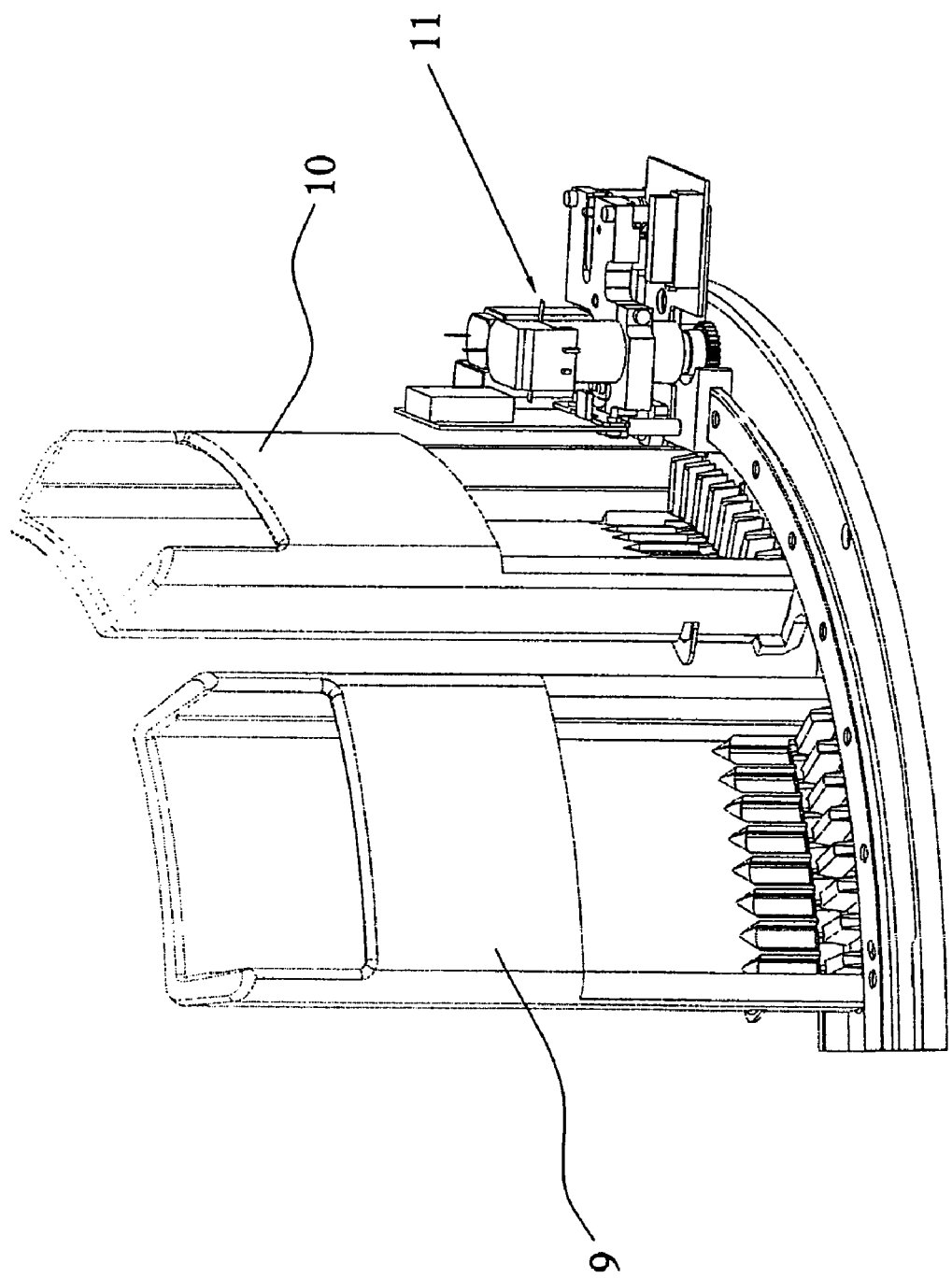
FIG. 4 shows a detail in perspective of the supports for containers or racks of reaction containers and of the pusher device.

As can be seen in FIGS. 1 and 2, the machine of the present invention comprises a module for the entry of reaction containers, indicated generally by the number 1, a module for the entry of samples 2, a reagent store 3, a sample arm device 4, a reagent arm device 5 and a scanning device 7. Each of said modules combines with the rest and with a central incubator 6, the assembly being controlled by means of a control unit with a built-in computer which can be monitored via the screen 8. The entry for reaction containers is the zone in which the operator introduces the disposable reaction containers on which dispensing and the reactions will be carried out. It is located adjacent to the incubator 6, arranged externally with respect to same, and comprises two supports 9 and 10, each intended for the introduction of a rack of reaction containers, being arranged in the shape of respective arcs of circumference that are concentric with respect to the incubator 6 and to a load introduction device 11 which contains the pusher for the reaction containers, which transfers the reaction containers, one by one, directly from the racks to one of the cavities of the incubator 6 which is free. When the reaction containers of one of the racks are used up, the pusher goes to the other rack and the user can replace the emptied one without stopping the process taking place, that is, there is continuous loading of the racks. Said racks, in a preferred case, contain eight columns, as can be seen in the detail of FIG. 21, which shows a support 12 which can assume the curved shape which can be seen in FIG. 22 and which comprises eight vertical channels such as 13, 13', 13" . . . intended to receive the reaction containers inside them, having at the bottom in one of its faces the apertures 14, 14', 14" . . . intended to permit the individual expulsion of the reaction containers contained inside it through the openings or apertures 15, 15', 15" . . . existing in the part opposed to the first ones. The apertures 15, 15', 15" are slightly narrower than the reaction containers so that the latter can always remain held in the rack except when they are pushed by the pusher device 11. When a reaction container is withdrawn by gravity from one of the columns 13, another reaction container becomes available in the lower part of the rack until the reaction containers of the column are used up.

Preferably, the eight columns of each rack are joined by a thin plate 16 at one face, remaining loose on the other face, so that they can curve as is shown in FIG. 22. The rack is preferably made of a transparent semi-rigid material and is equipped with an upper lid (not shown) and in the lower end has small flanges 17 which prevent the reaction containers from falling. The racks are introduced vertically and through the lower end of each column enter turrets on which the reaction containers rest so that they can slide for their withdrawal.

On the plate 16 adheres a label (not shown) which contains an electronic system or "tag" on which information can be recorded and recovered by means of an antenna (not shown) contained in the apparatus. By the use of this device it is possible to check at any time the number of reaction containers available, said information being updated each time that a reaction container is extracted from the rack. In addition, this device may contain information regarding the manufacturing batch or specific characteristics of the reaction containers or the rack. The tag may contain this or other information in coded form, in order to render impossible, practically, the voluntary modification or replication thereof by third persons, and in this way to prevent the use of the apparatus with racks or reaction containers different from the originals.

The sample entry module 2 is shown in greater detail in FIGS. 17 to 20, comprising a table 18 on which the supports 19 for the tubes of samples 20 move. Said table 18 is divided in practice into two zones, one for the entry of the samples and the other for the exit of same, both having been shown by way of example by means of the corresponding vectors 21 and 22. The individual supports 19 have means for the self-centered fastening of the tubes of samples 20, as will be explained, and at the bottom they have magnetic elements which interact with movable magnetic elements 23 and 24, located beneath the table 18 and which allow automatic entry, by means of the aforesaid magnetic means, of the tubes of samples from the entry of the table 18 to the feeder, in the form of an endless chain 25, provided with individual seats such as 26, 26', 26" in which the supports 19 fit in succession and are moved towards the sample-taking zone.

The supports of the tubes of samples can be seen in greater detail in FIGS. 9 to 15. Said supports 19 have a flat lower base 27 in which is associated a magnetic device 28, FIG. 13, capable of producing rotation on interacting with external magnetic means, therefore allowing the agitation of the tube of samples. The magnetic devices 28 also allow interaction with the magnetic devices 23 and 24 for having the tube supports to slide on the table 18. In addition, each of the supports 19 has three rotatory arms 29, 30 and 31 (FIG. 11) between which a tube of samples 20 can be held fast, FIGS. 14, 15 and 16. Said arms 29, 30 and 31 are rotatable on their lower axes 32, 33 and 34, which extend in toothed sectors 35, 36 and 37 which are meshed in the same central crown gear 38. By means of this arrangement, the self-centering of the tube 20 in the support 19 is ensured, the tube 20 remaining under all circumstances in a coaxial arrangement with respect to the support 19.

Figure 5:
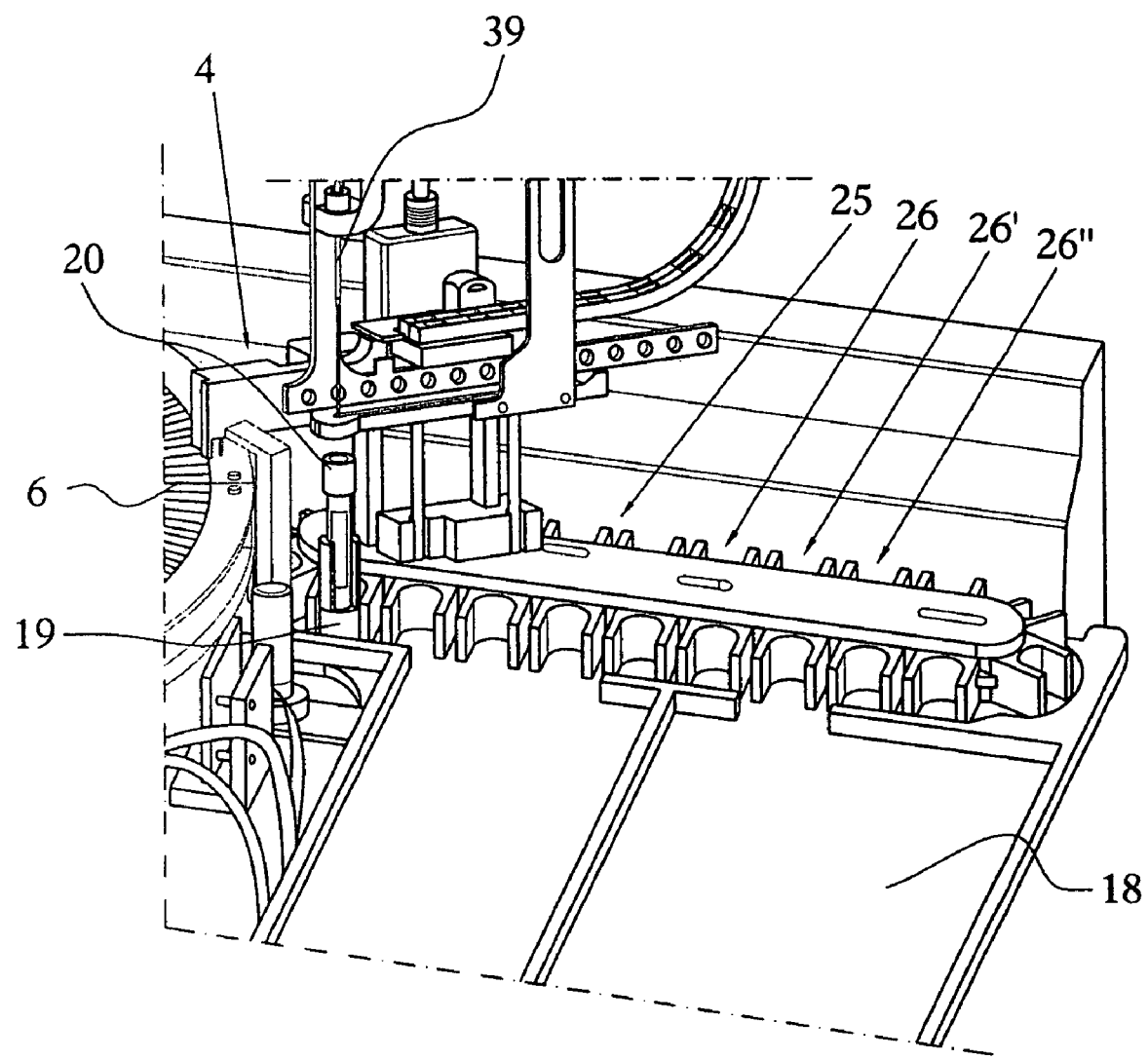
FIG. 5 shows a perspective view of the entry device and of the sample arm device.
Figure 6:
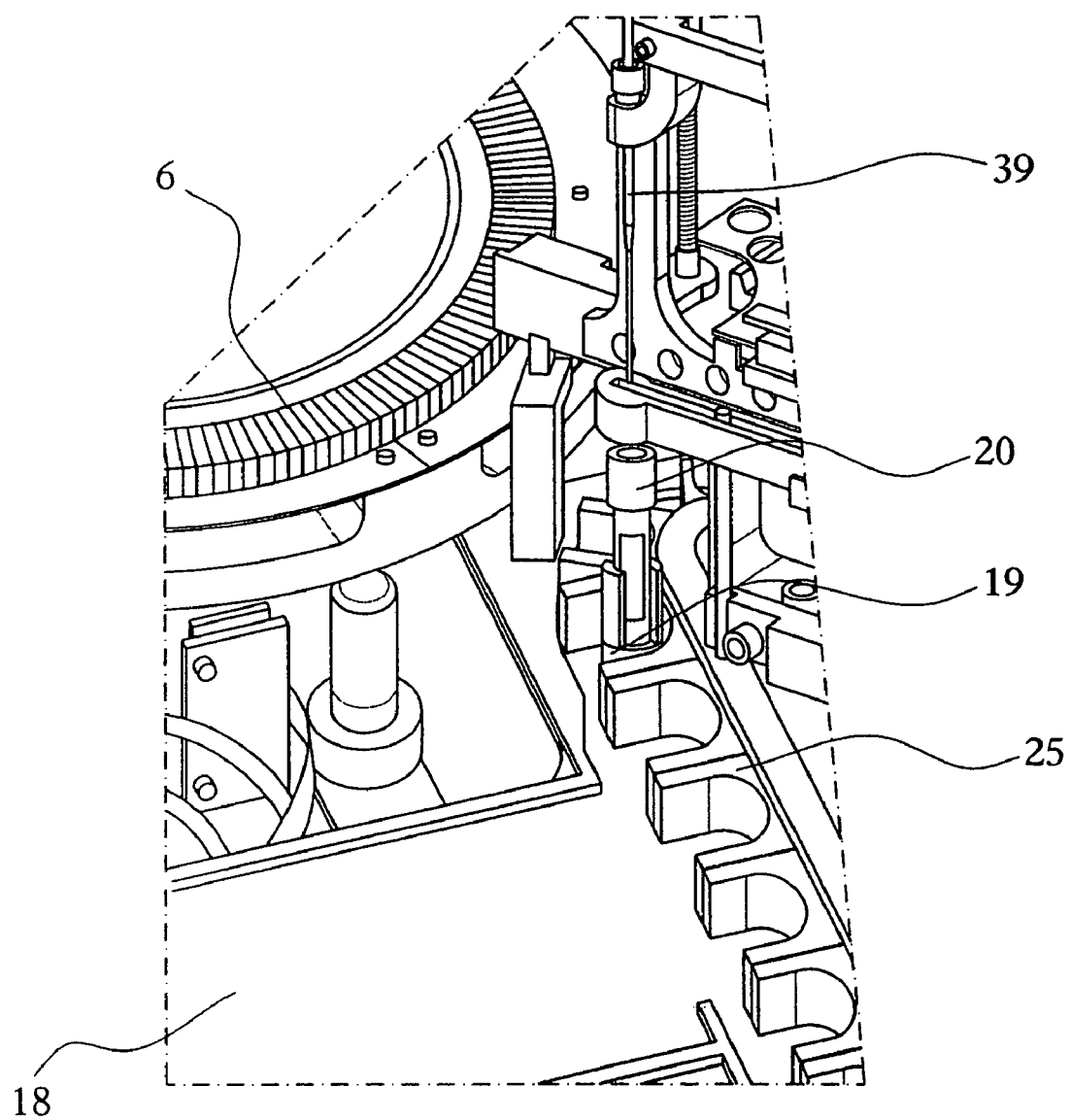
FIG. 6 shows on an enlarged scale a detail of the same sample arm.

The sample arm device 4 can be seen in detail in FIGS. 5 and 6. Said sample arm is intended to collect the sample from the tubes stopped by the device 25 in one or more positions of the incubator 6, and by rotation of the latter, in any of the reaction containers deposited in the incubator. Dispensing is effected by means of a probe 39 connected to a suitable fluid system which is capable of perforating stoppers of tubes of sample or other reagents. The sample arm is also capable of aspirating a diluent from the desired position of the reagent store 3, dispensing it at the corresponding position of the incubator 6. The three positions which the sample arm can reach, that is, the pipetting point, shown correspondingly with the tube of samples 19 in FIG. 5, the dispensing point and the point of aspiration of the diluent, are arranged in a straight line so that the arm 4 displaces the probe linearly, the probe also being provided with vertical movement for access to the interior of the tubes of samples, reaction containers and vials of reagents.

The reagent store 3 is formed by a circular ring internally concentric with respect to the incubator 6. It preferably comprises a plurality of removable small steps provided with circular movement to accomodate the reagents and diluents necessary for the sample analyses. It may be equipped with a cooling system for maintaining the reagents at the temperature necessary for preserving them. The steps have various types of seats for tubes and vials of different sizes depending on the presentation of the reagents and diluents provided preferably, but not exclusively, with a self-centered system which avoids the use of adaptors. A plurality of positions of reagents are provided with magnetic agitation for the reagents that require it.

The arm device 5 for the reagents is located concentrically in the interior of the reagent carousel, FIG. 2, and has freedom of movement in a polar direction, that is, radial and angular, thereby making it possible to have access to any position of the store of reagents for the aspiration of same and to any position of the incubator 6 or of the scanner 7 for dispensing the aspirated reagent. Aspiration is effected by means of a probe 40, preferably tempered, and capable of vertical movement. It has a radial actuator 41 for pushing reaction containers from the incubator to the scanner 7. The polar displacement may be limited in order to avoid collisions with the sample arm device 4.

Figure 8:
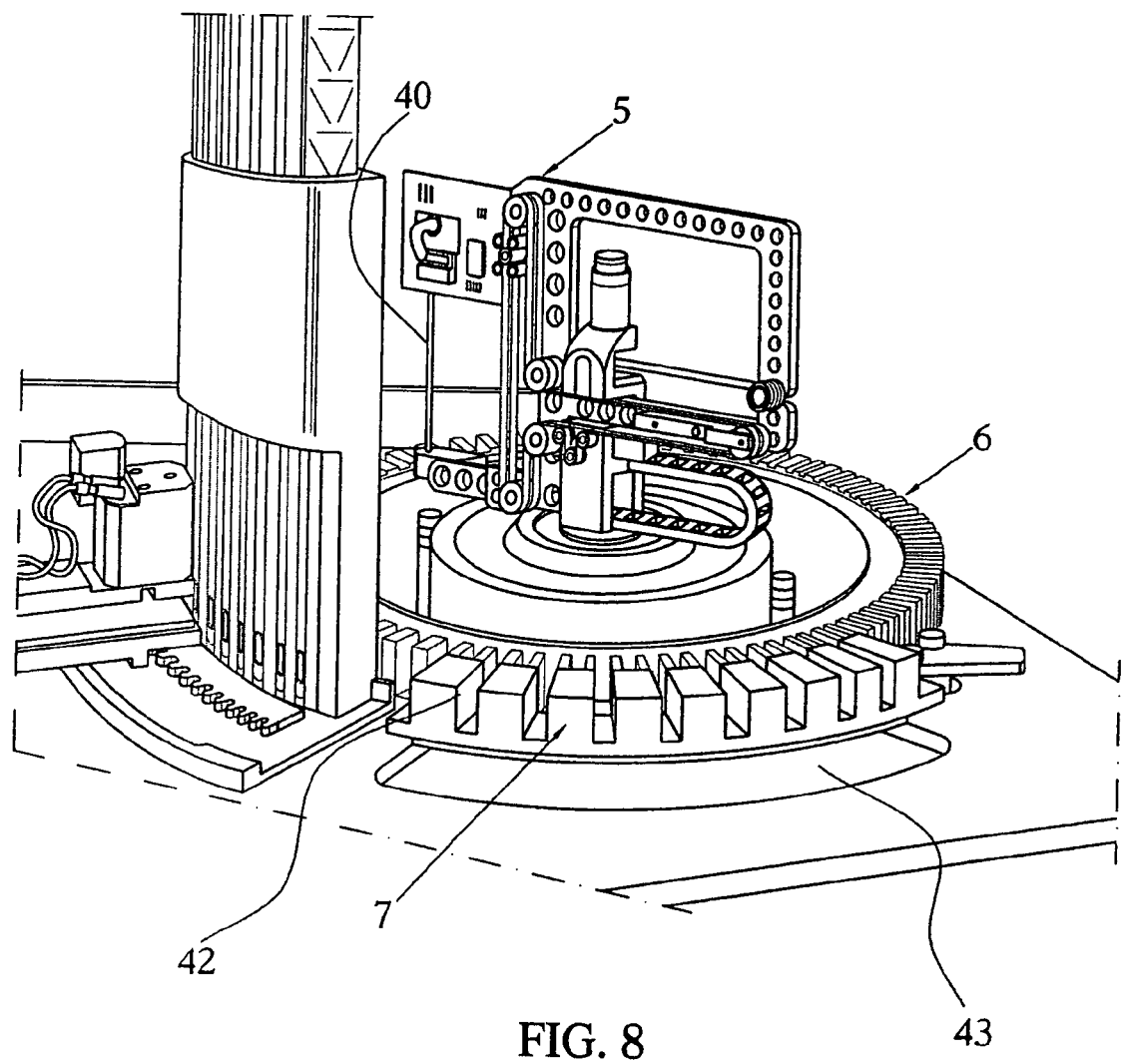
FIG. 8 shows a perspective view in which can be seen the carousel and the scanning zone.
Figure 9:
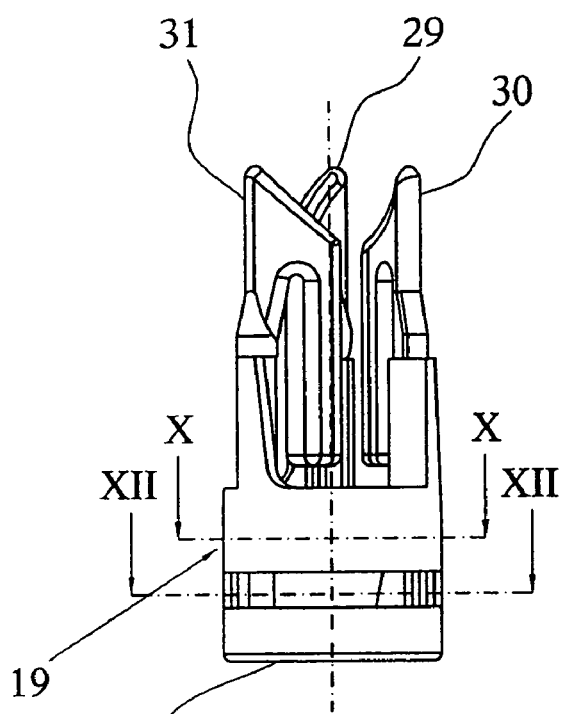
FIG. 9 shows a view in elevation of a support for the introduction of tubes of samples.
Figure 10:
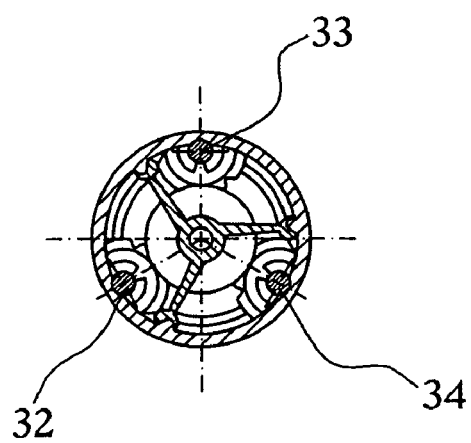
FIGS. 10, 11 and 12 are respective details of the same support for tubes of samples.
Figure 11:
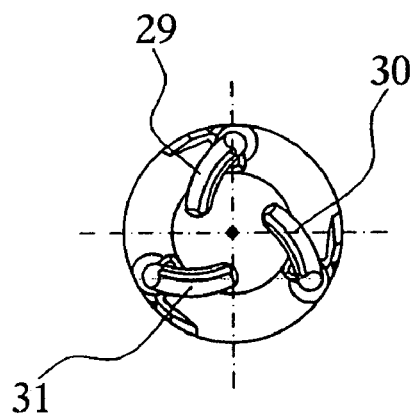
Figure 12:
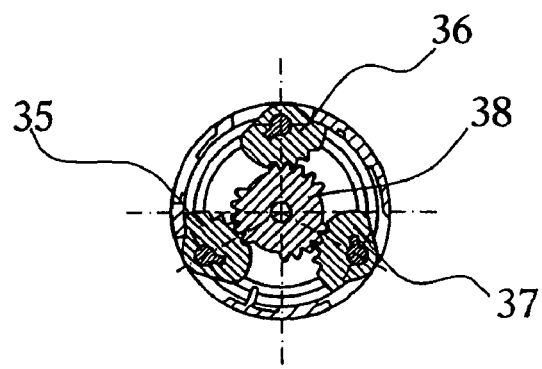
Figure 13:
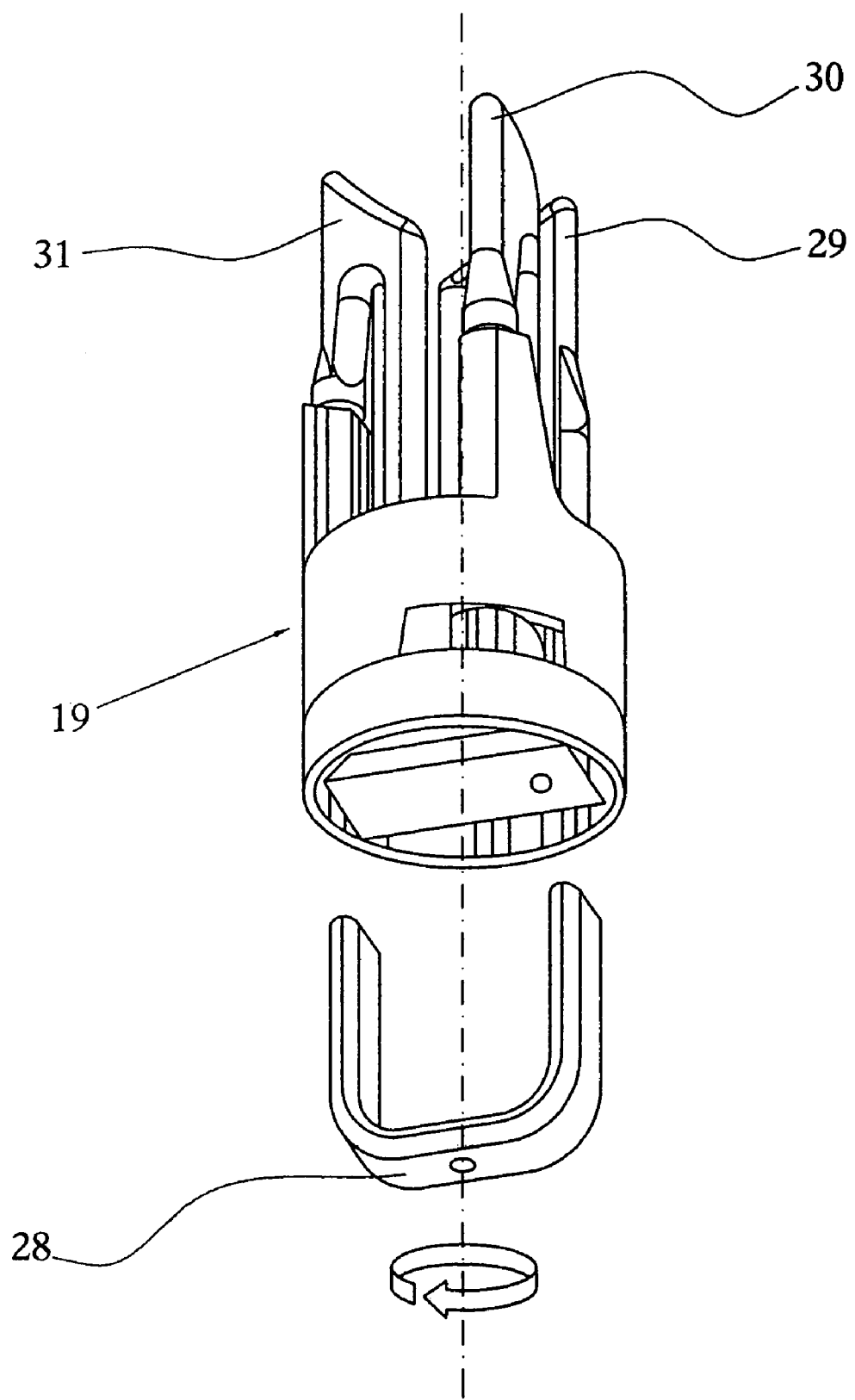
FIG. 13 shows a perspective view of the support for samples with the magnetic element disassembled.

The scanner 7 is in the shape of an arc of a circular ring concentric with the incubator 6, FIGS. 1, 2 and 8. Preferably, it has a multiplicity of seats in the form of radial channels 42 open at both ends to allow the introduction of the reaction containers from the incubator and their exit through the other end. The channels are covered by a lid (not shown) which is partially uncovered to allow the dispensing of additional reagents. Said channels 42 face the same number of cavities of the incubator 6, so that the reaction containers can be transferred directly from the incubator when they are prepared for scanning. The transfer is effected by pushing by means of the radial actuator 41 of the reagent arm 5 towards one of the channels 42 of the scanner 7. The reaction container which enters for scanning pushes out the reaction container which has already been scanned previously, through the same channel towards a waste container, through the aperture 43 provided for this purpose. The scanner 7 is equipped with an optical system which makes it possible to pass a beam of light through each of the reaction containers, picking up the transmitted light and being capable of processing it subsequently in order to obtain optical information on the reaction which has taken place in each reaction container. The readings are independent and may be taken simultaneously and asynchronously.

One of the essential advantages of the apparatus of the present invention is the division into a series of modules which carry out individual functions and which work in a coordinated but independent manner with one another, simultaneous in time. In addition, the modules which interact are contiguous with one another so that the reaction containers can be loaded in a plurality of positions, independently and simultaneously with other operations. Likewise, having two loading devices available for reaction containers allows continuous loading of the racks of reaction containers without holding up the process of the apparatus.

Figure 7:
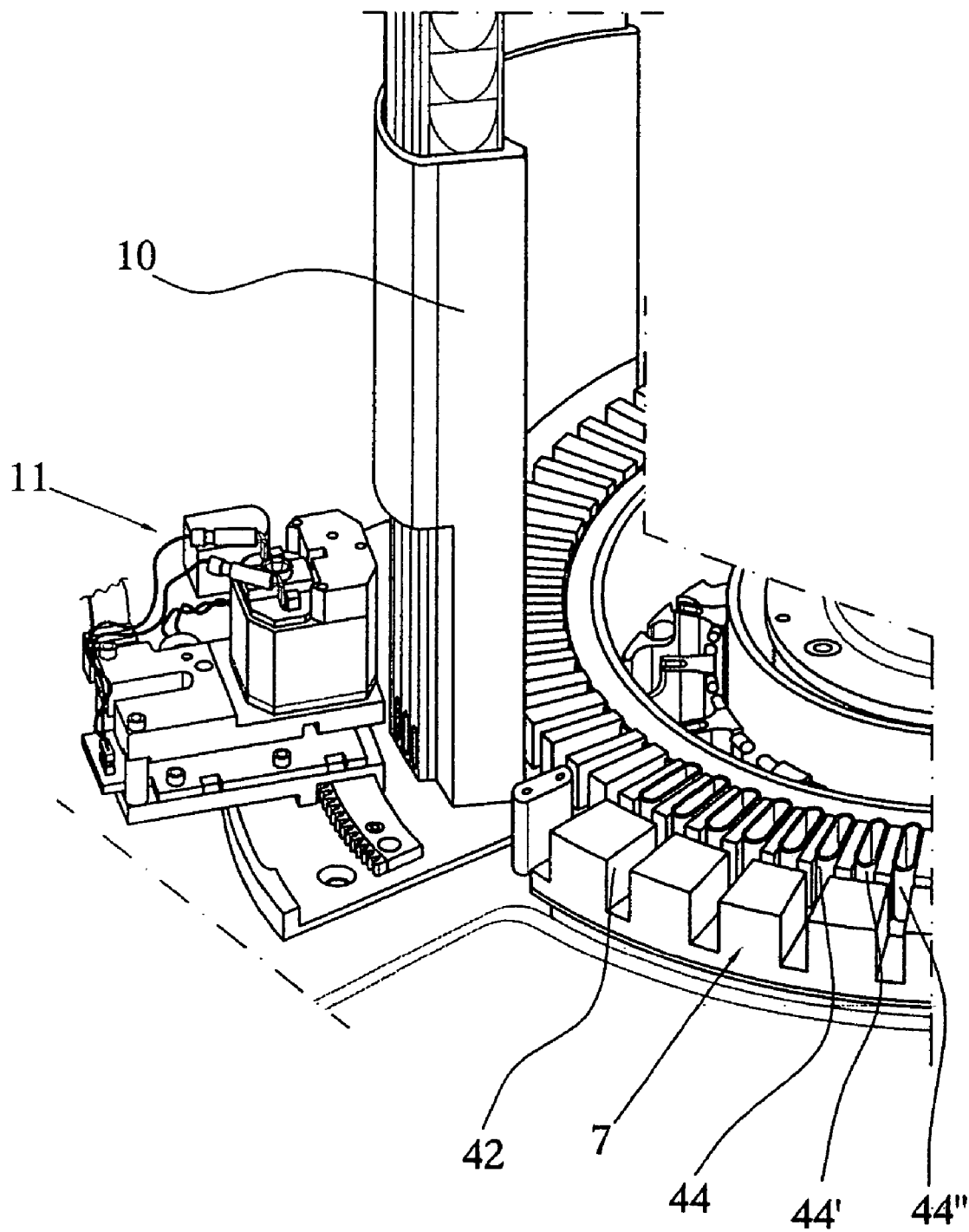
FIG. 7 shows a perspective view of the carousel and of the reaction container pusher device positioned with respect to the supports for the reaction containers.

Moreover, dispensing, both of samples and of reagents, is carried out directly in the incubator 6, which takes the shape of a circular ring, the remainder of the modules being located around the latter or inside it, thus optimising the space occupied by the assembly. The reaction containers may be transferred between the entry for the reaction containers and the scanner contiguous with the incubator merely by means of a pushing movement, as may be observed by the arrangement of the reaction containers 44, 44', 44", FIG. 7, which minimises the distance for the transport of the reaction containers between modules, reducing the transport time and therefore increasing the speed of working, and further avoiding any complications of the transport system. The pushing system also makes it easy to implement the continuous loading system of reaction containers and the random access of any reaction container.

Likewise, the incubator provided with movement reduces the complexity of the sample arm device 4, since the incubator 6 is what places the reaction container 44 in the position for dispensing the sample and enables the sample arm device 4 to move horizontally in a single direction, rendering the mechanism simpler and minimising the problems of overlapping with the reagent arm 5. The movement of the incubator 6 allows access to any cavity of the carousel for seating reaction containers.

The configuration described allows optimum execution of different tests simultaneously.

1. Reaction containers can be preloaded into the incubator 6 so that there are always empty reaction containers available.
2. As samples arrive with different test requests, the sample arm 4 dilutes them or dispenses them into as many empty reaction containers as necessary depending on the individual requests for each sample.
3. The reaction containers may remain in different phases of the test for the incubation time defined for each phase and test in the incubator 6; it does not matter if some tests require longer incubation than others since, as each one finishes, the following phase can be linked on an individualised basis and not necessarily in the order in which the tests started.
4. The reagent arm 5 can dispense the necessary reagents into any reaction container at any time, since it is capable of polar movement and can move to the reaction container whatever its position.
5. Said reagent arm 5 can absorb any reagent from any position, since the reagents are also capable of an independent circular movement for greater flexibility.
6. The transfer of the reaction container to the scanner 7 may take place from any position of the incubator 6 to any position of the scanner 7.
7. Each scan can begin whenever desired, for the time desired. All this, and with the logical mechanical limitations, permits maximum flexibility for randomly carrying out tests of different characteristics on each sample.

In the operating process of the apparatus of the invention, the operator, prior to and during the execution of the tests, must carry out a series of operations. In order to start the tests, there must be in the reagent store 3 all the reagents necessary for the tests which may be requested. He must also maintain the containers of liquids. He also has to place racks of reaction containers in the corresponding magazines 9 and 10.

The user introduces the tubes of samples to be processed and removes those already processed in the sample entry module 2.

The reaction container loading system automatically maintains a convenient number of reaction containers permanently available in the incubator 6.

The sample entry system 2 identifies the tubes of samples and their supports by means of a barcode and it is preferably communicated to a remote computer or host in order to obtain the tests to be carried out on each sample. Alternatively, the list of tests to be carried out may be recorded on the actual computer of the analysis system.

According to the test being carried out on each reaction container, as the required incubation times are completed, the reagent arm 5 will dispense the appropriate reagents into the corresponding reaction containers.

When the appropriate moment arrives for each test, the reaction container transfers to a position of the scanner 7 where more reagents may additionally be dispensed.

The scanner 7 carries out the simultaneous and asynchronous optical scanning of the reactions in progress.

Preferably, the computer of the analysis system sends to the host the results of the tests when they are completed.

The present invention has been described and shown on the basis of a preferred example thereof. However, it will be understood that the invention should not be regarded as limited to said concrete embodiment shown in the drawings and explained in the description, since any equivalent embodiments will obviously be included within the scope of the invention, which will be limited solely by the appended claims.

The invention claimed is:

1. An apparatus for the automated clinical analysis of samples comprising:

a circular reagent store having concentric rings for carrying reagent containers;

a rotatory carousel having grooves for carrying reaction containers;

a reaction container entry device adjacent the rotatory carousel for supplying the reaction containers by means of a detachable rack containing the reaction containers, wherein the reaction container entry device comprises a reaction container pushing device for feeding the rotatory carousel by pushing the reaction containers from the detachable rack towards the grooves of the rotatory carousel;

a reagent arm device in a radial arrangement with respect to the circular reagent store, being capable of polar displacement for linking the reagent containers and the reaction containers and for moving the reaction containers out of the rotatory carousel;

a scanning device concentric with the rotatory carousel capable of scanning reaction containers moved into the scanning device from the rotatory carousel by the reagent arm device;

a linear arm device capable of rectilinear movement for linking tubes carrying samples with the reaction containers;

a table for the entry and exit of supports for the tubes carrying samples, the table having a means for automatic displacement of said supports towards a continuous feeder for feeding the supports towards the linear arm device for pipetting the samples to the reaction containers; and a control unit for controlling the apparatus, wherein the reagent arm device comprises an end pushing device for pushing the reaction containers out of the rotatory carousel for removal.

2. The apparatus for the automated clinical analysis of samples according to claim 1, wherein the reaction container entry device comprises two arcuate supports adjacent to the rotatory carousel, each of said arcuate supports being capable of receiving the detachable rack containing reaction containers, the detachable rack being accessible to the reaction container pushing device which is displaceable over a toothed segment radial with respect to the circular reagent store and the rotatory carousel.

3. The apparatus for the automated clinical analysis of samples according to claim 2, wherein the detachable rack comprise a plurality of straight columns joined at one face by means of a laminar wall, the columns thereby being capable of curving on said face in order to adapt to the arcuate supports, a bottom of each column having retaining flanges for retaining the reaction containers, and apertures for allowing the reaction containers to exit the detachable rack.

4. The apparatus for the automated clinical analysis of samples according to claim 3, wherein each column comprises aligned apertures in an outer face and in an inner face, the aligned apertures being of smaller dimensions than the reaction containers.

5. The apparatus for the automated clinical analysis of samples according to claim 1, wherein the temperatures of the reagent store and the rotatory carousel are independently thermostatically controlled by the control unit.

6. The apparatus for the automated clinical analysis of samples according to claim 1, wherein the table for the entry and exit of supports for the tubes carrying samples comprises a magnetic means for passing the supports for the tubes carrying samples to a continuous feeder equipped with a plurality of seats for the supports, the plurality of seats being moveable on the table to transport the tubes carrying samples to and from the linear arm device.

7. The apparatus for the automated clinical analysis of samples according to claim 6, wherein each support for the tubes carrying samples comprises a self-centering receptacle for one of the tubes carrying samples and a magnetic means on a base which permits interaction with the magnetic means of the table.

8. The apparatus for the automated clinical analysis of samples according to claim 7, wherein the self-centering receptacle comprises a plurality of vertical arms operative to establish contact with one of the tubes carrying samples, said vertical arms being rotatable synchronously to thereby produce a self-centering effect.

9. The apparatus for the automated clinical analysis of samples according to claim 8, wherein the vertical arms are rotatable about a lower axes and extend in toothed segments which mesh with a gearwheel arranged centrally to produce the synchronisation of rotation of the vertical arms.

10. The apparatus for the automated clinical analysis of samples according to claim 1, wherein the linear arm device comprises a longitudinally displaceable arm carrying a probe, the arm being operative to collect a sample by passing the probe through a stopper covering a top of one of the tubes carrying samples to thereby extract the sample by pipetting, the arm being further operative to transport the collected sample to one of the reaction containers.

11. An apparatus for the automated clinical analysis of samples comprising:

a circular reagent store having concentric rings for carrying reagent containers;

a rotatory carousel having grooves for carrying reaction containers;

a reaction container entry device adjacent the rotatory carousel for supplying the reaction containers by means of a detachable rack containing the reaction containers, wherein the reaction container entry device comprises a reaction container pushing device for feeding the rotatory carousel by pushing the reaction containers from the detachable rack towards the grooves of the rotatory carousel;

a reagent arm device in a radial arrangement with respect to the circular reagent store, being capable of polar displacement for linking the reagent containers and the reaction containers and for moving the reaction containers out of the rotatory carousel;

a scanning device concentric with the rotatory carousel capable of scanning reaction containers moved into the scanning device from the rotatory carousel by the reagent arm device;

a linear arm device capable of rectilinear movement for linking tubes carrying samples with the reaction containers;

a table for the entry and exit of supports for the tubes carrying samples, the table having a means for automatic displacement of said supports towards a continuous feeder for feeding the supports towards the linear arm device for pipetting the samples to the reaction containers; and a control unit for controlling the apparatus, wherein the reagent arm device has a radial structure with respect to the circular reagent store and further comprises a means for rotation and radial displacement of the reagent arm and a probe for collecting reagents to be deposited in at least one of the reaction containers, and wherein the reagent arm device has an end pushing device for pushing the reaction containers out of the rotatory carousel for removal.

\* \* \* \* \*